United States Patent [19]
Lapis et al.

[11] Patent Number: 4,874,765
[45] Date of Patent: Oct. 17, 1989

[54] 1,4-DISUBSTITUTED PIPERAZINES HAVING DOPAMINERGIC ACTIVITY

[75] Inventors: Erzsébet Lapis; Edit Tóth, both of Budapest; Béla Kiss, Vecsés; József Törley, Budapest; Éva Pálosi, Budapest; István Hajdu, Budapest; László Szporny, Budapest; Dóra Groó, Budapest; István Laszlovszky, Budapest, all of Hungary

[73] Assignee: Richter Gedeon Vegyeszeti Gyar, Budapest, Hungary

[21] Appl. No.: 41,206

[22] Filed: Apr. 22, 1987

[30] Foreign Application Priority Data

Apr. 22, 1986 [HU] Hungary ............. 2251/1749/86

[51] Int. Cl.$^4$ ............. A61K 31/495; C07D 295/08; C07D 295/10
[52] U.S. Cl. ............. 514/255; 544/386; 544/397
[58] Field of Search ............. 544/397, 392, 386; 514/255

[56] References Cited

U.S. PATENT DOCUMENTS

2,988,551 6/1961 Morren ............. 544/397

FOREIGN PATENT DOCUMENTS

549420 7/1956 Belgium .
551032 3/1957 Belgium .
99148 1/1984 European Pat. Off. ............. 544/397
2276824 1/1967 France .
837986 6/1960 United Kingdom ............. 544/397

OTHER PUBLICATIONS

Vadodaria et al., J. Med. Chem. 1969, 12, 860–5.
Morren et al., New derivatives of 1,4–disubstituted piperazines, CA: vol. 52, 1958, 12873–12874.
Morren, Piperazine derivatives, eq. BE 551,032, CA, vol. 53, 1959, 20101–20102.
Morren, Piperazine derivatives, CA vol. 54, 12169.
Vadodaria et al., Synthesis and Central Nervous System Depressant Activity of New Piperazine Derivatives and Related Compounds, CA vol. 71, 1969, 101817t.
Patel et al., Antimicrobial Activity of Piperazine Derivatives and Related Compounds.
Melon et al., 1,4–disubstituted piperazine derivatives eq. Fr. 2,276,824, CA: vol. 85, 1976, 160163p.
Gist-Brocades, Piperazine Derivatives; and Pharmaceutical Comp. Containing Them. CA, vol. 100, 1984, 191909u.
Carlsson (1988) Perspectives in Psychopharmacology Collection of Papers in Honor of E. Usdin. Alan L. Riss, Inc. pp. 209–223.
Gottries (1985) Psychopharmacology 86:245–252.
Morren et al. (1957) Ind. Chim. belge 22:409–420.

Primary Examiner—Cecilia Shen
Attorney, Agent, or Firm—Keil & Weinkauf

[57] ABSTRACT

The invention relates to novel 1,4-disubstituted piperazine derivatives of the general formula (I), pharmaceutically acceptable acid addition and quaternary ammonium salts thereof, pharmaceutical compositions containing them and a process for their preparation. In the general formula (I)

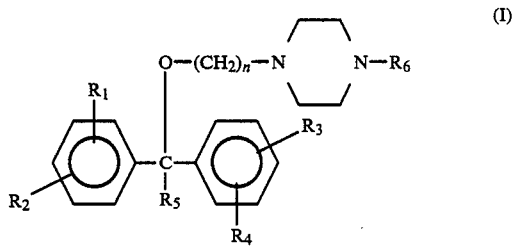

$R_1$, $R_2$, $R_3$ and $R_4$ are the same or different and stand for hydrogen or halogen or a trihalomethyl, lower alkyl, lower alkoxy, nitro, hydroxyl, aralkyloxy or an 1-(2-propenyl-4-piperazinyl) group;
$R_5$ stands for hydrogen or a $C_{1-4}$ alkyl group;
$R_6$ represents a $C_{3-6}$ alkyl, alkenyl, alkynyl group or a

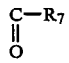

group, wherein
$R_7$ means a $C_{2-5}$ alkyl, alkenyl or alkinyl group; and is 2 or 3,
with the provisos that:
$R_6$ is different from isopropyl, n-butyl and isobutyl group when $R_2$, $R_3$, $R_4$ and $R_5$ stand for hydrogen, $R_1$ means 2-chloro and n is 2;
$R_6$ is different from isopropyl group when $R_2$, $R_3$, $R_4$ and $R_5$ stand for hydrogen, $R_1$ means 2-chloro and n is 2; or when $R_2$, $R_3$, $R_4$ and $R_5$ stand for hydrogen, $R_1$ means 2-methyl group and n is 2; and
$R_6$ is different from propionyl group when $R_1$, $R_2$, $R_3$, $R_4$ and $R_5$ are hydrogen and n means 2.

The compounds of the general formula (I) are therapeutically useful for the treatment of diseases arising from a hypofunction of the dopaminergic system.

4 Claims, No Drawings

1,4-DISUBSTITUTED PIPERAZINES HAVING DOPAMINERGIC ACTIVITY

The invention relates to novel diphenylmethoxyalkylpiperazine derivatives of the general formula (I).

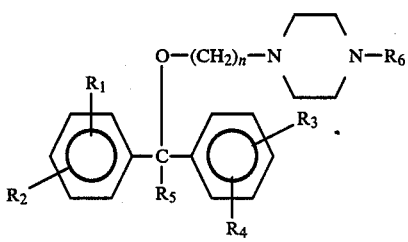

wherein
$R_1$, $R_2$, $R_3$ and $R_4$ are the same or different and stand for hydrogen or halogen or a trihalomethyl, lower alkyl, lower alkoxy, nitro, hydroxyl, aralkyloxy or an 1-(2-propenyl-4-piperazinyl) group;
$R_5$ stands for hydrogen or a $C_{1-4}$ alkyl group; represents a $C_{3-6}$ alkyl, alkenyl, alkynyl group or a

group, wherein $R_7$ means a $C_{2-5}$ alkyl, alkenyl or alkinyl group; and
n is 2 or 3, with the provisos that:
$R_6$ is different from isopropyl, n-butyl and isobutyl group when $R_2$, $R_3$, $R_4$ and $R_5$ stand for hydrogen, $R_1$ means 2-chloro and n is 2;
$R_6$ is different from isopropyl group when $R_2$, $R_3$, $R_4$ and $R_5$ stand for hydrogen, $R_1$ means 2-chloro and n is 3; or when $R_2$, $R_3$, $R_4$ and $R_5$ stand for hydrogen, $R_1$ means 2-methyl group and n is 2; and
$R_6$ is different from propionyl group when $R_1$, $R_2$, $R_3$, $R_4$ and $R_5$ are hydrogen and n means 2,
as well as their pharmaceutically acceptable acid addition and quaternary ammonium salts and pharmaceutical preparations containing these compounds.

According to an other aspect of the invention, there is provided a process for the preparation of the new compounds of the general formula (I) and acid addition salts and quaternary ammonium salts thereof.

The preparation of the disclaimed known compounds is described in the following literature references: H. G. Morren: Ind. Chim. belge 22, 409 (1957) (CA 52, 12873i); Belgian patent specifications Nos. 551,032 and 549,420 (CA 53, 2010f and CA 54, 12169a, respectively); as well as French patent specification No. 2,276,824 (CA, 85, 161063p). According to pharmacological studies the above compounds possess a strong ulcer-in-hibiting action in addition to a weak antihistamine effect without any other pharmacological activity; the compound reported in the French patent specification shows an antitussive effect.

Now it has surprisingly been found that the novel compounds of the invention of the general formula (I) show a strong, selective dopaminergic activity on the central nervous system and thus they are useful for treating diseases occurring as a consequence of the degeneration and/or hypofunction of the dopaminergic system, such as depression, parkinsonism, several neuroendocrine illnesses, "ageing", impotence and the like.

The dopaminergic activity of the compounds of the invention was determined by in vitro and in vivo animals tests. On the examination of the in vivo activity, the protective capability of the compounds against the neurotoxic effect of 1-methyl-4-phenyl-1,2,3,6-tetrahydropyridine (MPTP) was also studied. In 1979 it was reported that MPTP causes the degeneration of the dopaminergic system in men and monkeys [G. C. Davis et al.: Psychiat. Res 1, 249 (1979; R. S. Burns et al.; Proc. Natl. Acad. Sci (USA), 80, 4546 (1983)]; the selective dopaminergic system-damaging effect on mice of this compound was also shown [see e.g. H. Hallman et al.: Eur J. Pharmacol. 97, 133 (1984); E. Pileblad et al.: Neuropharmacol. 24, 689 (1986)]. The selective dopaminergic system-damaging effect caused by MPTP on test animals can be considered to be a process analogous to the degenerative and hypofunctional diseases of the human dopaminergic system and thus it is a suitable model for investigating compounds useful for the therapeutical treatment of diseases connected with the pathological functioning of the dopaminergic system [A. J. Bradbury et al.: The Lancet 1985, 1444; H. Przuntek et al.: Life Sci. 37, 1195 (1985).

For these investigations male CFY mice (LATI, Gödöllö, Hungary) weighing 20-25 g were used. The compounds to be tested were homogenized in 1% Tween 80 solution and administered to the animals in a dose of 0.1 mmole/kg (in the route given in the Table) 1 hour before administering MPTP. MPTP was freshly dissolved in physiological saline solution and subcutaneously given to the mice in a dose of 70 mg/kg. 72 to 96 hours after the administration of MPTP the animals were killed by decapitation, their brain was rapidly removed, cooled in an ice-cold physiological saline solution, the striatum was excised and refrigerated in dry ice.

The tissues (in a refrigerated condition) were weighed and homogenized in 1 ml of 0.4N perchloric acid solution containing 0.5% of $Na_2S_2O_5$, 0.25% of $Na_2EDTA$ and 100 ng of M-methyldopamine (internal standard for the determination of catecholamines) in an Ultra-Turrax equipment. The homogenate was centrifuged at 4° C. at 20,000 g for 10 minutes, then 0.8 ml of the supernatent was taken out. After adding 20 mg of activated aluminum oxide, the pH value of the solution was adjusted to 8 by adding 0.5M Tris solution and the tubes were shaken for 20 minutes. The aluminium oxide was settled, the supernatent was removed by suction and washed 3 times with 5 ml of distilled water each. The catecholamines adsorbed on the aluminium oxide were eluted with 1 ml of 0.05N perchloric acid. From a part of the eluate, dopamine was determined by using high pressure liquid chromatography by means of electrochemical detection (Labor MIM Oe-320 pump, 4×150 mm Nucleosil 5 C-18 analytical column and 4×20 mm Nucleosil 5 C-18 supplementary column; electrochemical detector fitted with a glassy-carbon working electrode and an $Ag/AgCl_2$ reference electrode; Eltron potentiostat, LKB 2110 2-channel recorder; with an oxidation potential of 600 mV and as mobile phase 0.1M $NaH_2PO_4$, 1 mM $Na_2EDTA$, 1 mM octanesulfonic acid containing 8.5% of acetonitrile; flow rate 1 ml/minute).

A decrease by 50 to 60% in the striatum dopamine level can be achieved by using the above method. The protection against the dopamine decrease induced by MPTP was calculated as follows:

$$\% \text{ inhibition} = \frac{(\text{treated with the compound} + \textit{MPTP}) - (\text{treated with } \textit{MPTP})}{(\text{control}) - (\text{treated with } \textit{MPTP})} \times 100$$

As a referenced drug, trihexyphenidyl hydrochloride ($\alpha$-cyclohexyl-$\alpha$-phenyl-1-piperidinepropanol hydrochloride) was used in a dose of 10 mg/kg (<0.1 mmole/kg). The animals perished on administration of a higher dose. The results are summarized in the Table.

In the Table, the following abbreviations are used:
MPTP: 1-methyl-4-phenyl-1,2,3,6-tetrahydropyridine hydrochloride
DA: dopamine
n: number of the animals
i.p.: intraperitoneal(ly)
o.p.: oral(ly)

1. 1-[2[bis(4-fluorophenyl)methoxy]ethyl]-4-(2-propenyl)-piperazine
2. 2-[2-[bis(4-fluorophenyl)methoxy]ethyl]-4-propyl-piperazine
3. 1-[2-[(4-fluorophenyl)-phenylmethoxy]ethyl]-4-(2-propenyl)piperazine
4. 1-[2-[(4-chlorophenyl)-(4-fluorophenyl)methoxy]-ethyl]-4-(2-propenyl)piperazine
5. 1-[2-[(4-bromophenyl)-(4-fluorophenyl)methoxy]-ethyl]-4-(2-propenyl)piperazine
6. 1-[2-[bis(4-chlorophenyl)methoxy]ethyl]-4-(2-propenyl)piperazine
7. 1-[2-[(3,4-dichlorophenyl)-phenylmethoxy]ethyl]--4-(2-propenyl)-piperazine
8. 1-[2-[(4-chlorophenyl)-(4-flurophenyl)methoxy]-ethyl]-4-propyl-piperazine
9. 1-[2-[bis(4-flurophenyl)methoxy]ethyl]-4-butyl-piperazine
10. 1-[2-[1-bis(4-fluorophenyl)ethoxy]ethyl]-4-(2-propenyl)piperazine
11. 1-[2-[bis(4-fluorophenyl)methoxy]ethyl]-4-(1-oxohexyl)piperazine
12. 1-[2-[bis(4-fluorophenyl)methoxy]ethyl]-4-(2--propynyl)piperazine
13. 1-[2-[bis(4-fluorophenyl)methoxy]ethyl]-4-(2-methyl--2-propenyl)-piperazine
14. 1-[2-[bis(4-fluorophenyl)methoxy]ethyl]-4-(1-oxopropyl)piperazine
15. 1-[2-[(3,4-dichlorophenyl)-(phenylmethoxy)ethyl]--4-butylpiperazine
16. 1-[2-[(4-chlorophenyl)-(4-fluorophenyl)methoxy]-ethyl]-4-butylpiperazine
17. 1-[2-[bis(4-fluorophenyl)methoxy]ethyl]-4-hexylpiperazine The compounds Nos. 11 and 14 are monohydrochlorides, whereas other compounds were tested as dihydrochlorides.

TABLE

| Compound No. | Dose: 0.1 ml/kg; route of administration | DA decrease induced by MPTP % inhibition | | n |
|---|---|---|---|---|
| | | i.p. route | p.o. route | |
| 1 | p.o. | 98 | 100 | 7-7 |
| 2 | i.p. | 100 | | 7 |
| 3 | p.o. | | 100 | 7 |
| 4 | i.p. | 100 | | 7 |
| 5 | i.p. | 100 | | 7 |
| 6 | i.p. | 100 | | 7 |

TABLE-continued

| Compound No. | Dose: 0.1 ml/kg; route of administration | DA decrease induced by MPTP % inhibition | | n |
|---|---|---|---|---|
| | | i.p. route | p.o. route | |
| 7 | i.p. p.o. | 100 | 98 | 7-7 |
| 8 | i.p. | 95 | | 7 |
| 9 | i.p. | 100 | | 7 |
| 10 | i.p. | 89 | | 7 |
| 11 | i.p. | 82 | | 7 |
| 12 | p.o. | | 94 | 7 |
| 13 | p.o. | | 95 | 7 |
| 14 | p.o. | | 71 | 7 |
| 15 | i.p. | 98 | | 7 |
| 16 | p.o. | | 86 | 7 |
| 17 | p.o. | | 89 | 7 |
| Trihexyphenidyl.HCl | i.p. | 7 | | 7 |

It is obvious from the data of the Table that, when administered orally and/or intraperitoneally to the animals before the treatment with MPTP, the compounds of the general formula (I) are capable to inhibit in a high degree or completely the neurotoxic dopamine-depleting action of MPTP. In addition, the compounds of the general formula (I) possess an advantageously low toxicity. Thus, the novel compounds of the invention represent a valuable therapeutical tool for influencing clinical cases wherein a dopaminergic hypofunction exists as a consequence of the degeneration of the dopaminergic system or for other reasons.

According to the invention, the compounds of the general formula (I) are prepared by (a) reacting a compound of the general formula (II),

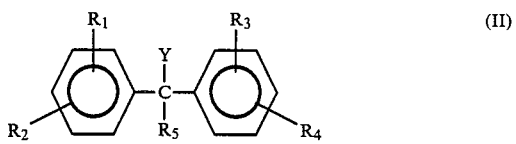

wherein $R_1$, $R_2$, $R_3$, $R_4$ and $R_5$ are as defined above and Y means an OM group (wherein M stands for an alkali metal, preferably lithium, potassium or sodium or an MgHlg group, wherein Hlg represents a halogen) or Y stands for a hydroxyl group, with a compound of the general formula (III),

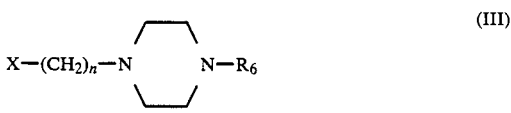

wherein $R_6$ and n are as defined above and X means a halogen or an alkylsulfonyloxy or arylsulfonyloxy group when Y means an OM group, or X stands for halogen or hydroxyl, alkylsulfonyloxy or arylsulfonyloxy group when Y means a hydroxyl group, or (b) reacting a compound of the general formula (IV).

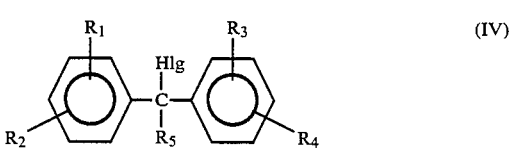

wherein $R_1$, $R_2$, $R_3$, $R_4$, $R_5$ and Hlg are as defined above, with a piperazine derivative of the general formula (V),

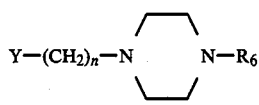
(V)

wherein $R_6$ and n are as defined above and Y stands for a hydroxyl or an OM' group, wherein M' represents an alkali metal, or (c) reacting a compound of the general formula (VI),

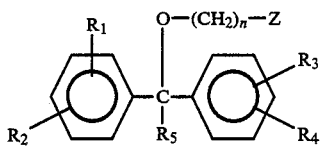
(VI)

wherein $R_1$, $R_2$, $R_3$, $R_4$, $R_5$ and n are as defined above and Z means a halogen or an alkylsulfonyloxy or arylsulfonyloxy group, with a piperazine derivative of the general formula (VII),

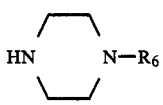
(VII)

wherein $R_6$ is as defined above, or (d) reacting a compound of the general formula (VIII),

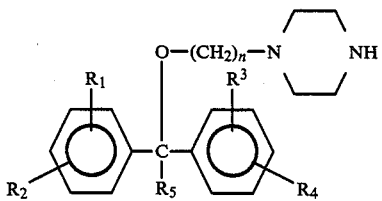
(VIII)

wherein $R_1$, $R_2$, $R_3$, $R_4$, $R_5$ and n are as defined above, with a compound of the general formula (IX), $Z - R_6$    (IX)

wherein Z and $R_6$ are as defined above, or (e) reacting a compound of the general formula (VIII), wherein $R_1$, $R_2$, $R_3$, $R_4$, $R_5$ and n are as defined above, with an aldehyde of the general formula (X),

(X)

wherein $R_7$ stands for a $C_{2-5}$ alkyl, alkenyl or alkynyl group, in the presence of a suitably selected reducing agent, or (f) reacting a compound of the general formula (VIII), wherein $R_1$, $R_2$, $R_3$, $R_4$, $R_5$ and n are as defined above, with a $C_{3-6}$ alkane-, alkene- or alkynecarboxylic acid derivative suitable for acylating and, if desired, reducing the thus-obtained compound of the general formula (I), wherein $R_1$, $R_2$, $R_3$, $R_4$, $R_5$ and n are as defined above and $R_6$ stands for a

group, wherein $R_7$ is as defined above, to a compound of the general formula (I), wherein $R_6$ means a $C_{3-6}$ alkyl, alkenyl or alkynyl group, or (g) reducing a compound of the general formula (I), wherein $R_1$, $R_2$, $R_3$, $R_4$, $R_5$ and n are as defined above and $R_6$ stands for a $C_{3-6}$ alkynyl group, if desired, partially or completely to a compound of the general formula (I), wherein $R_6$ represents a $C_{3-6}$ alkenyl or alkyl group and $R_1$, $R_2$, $R_3$, $R_4$, $R_5$ and n are as defined above, or (h) if desired, reducing a compound of the general formula (I), wherein $R_1$, $R_2$, $R_3$, $R_4$, $R_5$ and n are as defined above, whereas $R_6$ stands for a $C_{3-6}$ alkenyl group, to a compound of the general formula (I), wherein $R_6$ stands for a $C_{3-6}$ alkyl group, whereas $R_1$, $R_2$, $R_3$, $R_4$, $R_5$ and n are as defined above, or (i) reducing an acid amide of the general formula (XI),

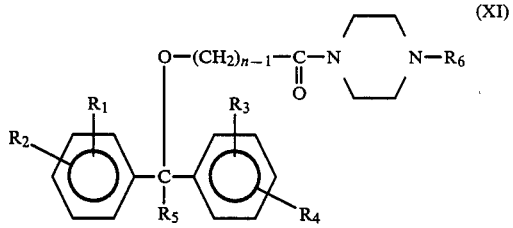
(XI)

wherein $R_1$, $R_2$, $R_3$, $R_4$, $R_5$ and n are as defined above and $R_6$ means a $C_{3-6}$ alkyl, alkenyl or alkynyl group, and, if desired, transforming a thus-obtained product prepared by using any one of processes (a) to (i) to an acid addition salt with an organic or inorganic acid or to a quaternary ammonium salt with a quaternizing agent or, if desired, transforming a product obtained in the form of an acid addition salt or a quaternary ammonium salt to the corresponding free base and/or, if desired, transforming a free base to its acid addition salt or quaternary ammonium salt.

The compounds of the general formula (I) may contain one or more asymmetric carbon atom(s) and may therefore exist in various stereoisomeric forms. Thus, the compounds of the general formula (I) according to the invention may be bases, acid addition salts, quaternary ammonium salts, racemates, separated optical isomers and the mixtures and solvates, e.g. hydrates, thereof.

The starting materials are known compounds or can be prepared by using processes known from the literature.

The benzhydrols of the general formula (II), wherein Y stands for a hydroxyl group or an OMgHlg group, wherein Hlg means a halogen, may be prepared e.g. by reacting the appropriate carbonyl compounds with Grignard reagents [see e.g.: M. S. Kharasch et al.:

Grignard Reactions of Nonmetallic Substances, Ed. Prentice-Hall Inc., pp. 138-143 (1954)].

The alcohols of the general formula (V) may be prepared e.g. by alkylating monosubstituted piperazines of the general formula (VII) with haloalkanols of the general formula Hlg—$(CH_2)_2$—OH, wherein n and Hlg are as defined above.

The halide derivatives of the general formula (III) may be prepared e.g. by reacting alcohols of the general formula (V) with thionyl chloride according to O. Hromatka et al. [Monatshefte 87, 701 (1956)].

The alkoxides of the general formulae (II) and (V), wherein Y means an OM' group and M' stands for an alkali metal, may be prepared from the appropriate alcohols [see e.g. Houben-Weyl: Methoden der Organischen Chemie VI/2, 6-34 (1963)] with alkali metals, alkali metal hydrides or alkali metal amides.

The preparation of the compounds of the general formula (IV) has been described e.g. by K. E. Hamlin at al. [J. Am. Chem. Soc. 71, 2731 (1949)] or by R. Baltzly et al. [J. Org. Chem. 14, 775 (1949)].

The ether compounds of the general formula (VI) may be prepared e.g. by using the method of Sugasawa [Org. Synth. 33, 11 (1953)].

The monosubstituted piperazine derivatives of the general formulae (VII) and (VIII) can be synthesized e.g. according to the methods of Kiichi Fujii [J. Pharm. Soc. Japan 74, 1049 (1954)], H. W. Stewart [J. Org. Chem. 13, 134 (1948)] or T. Irikura [J. Med. Chem. 11, 801 (1968)] as well as according to the Belgian patent specification No. 549,420.

The starting materials of the general formula (XI) can be prepared e.g. by reacting the alkoxides of the general formula (II) with compounds of the general formula (XII),

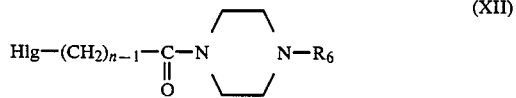

(XII)

wherein $R_6$, n and Hlg are as defined above, under the same conditions as defined in process (a). The compounds of the general formula (XII) can be synthetized e.g. according to the U.S. patent specification No. 3,041,341 (CA 57, 13778d).

According to process (a) of the invention, a compound of the general formula (II), wherein $R_1$, $R_2$, $R_3$, $R_4$ and $R_5$ are as defined above and Y stands for an OMgHlg group, wherein Hlg is halogen, is reacted with a piperazine derivative of the general formula (III), wherein $R_6$ and n are as defined above and X stands for a halogen or an alkylsulfonyloxy or arylsulfonyloxy group, in an anhydrous organic solvent which is inert to the reaction conditions. As a reactive derivative of the compound of the general formula (III), the mesylate, tosylate, preferably chloride or bromid thereof can be used. Suitably, this reaction is carried out under an inert gas such as nitrogen or argon. Useful solvents are e.g.: aliphatic or alicyclic ethers such as di(n-butyl)-ether, tetrahydrofuran, dioxane; aliphatic or aromatic hydrocarbons such as n-hexane, ligroin, benzene, toluene or xylene; as well as dimethylsulfoxide, hexamethylphosphoramide and the mixtures of these solvents.

When Y in the compound of the general formula (II) means hydroxyl group and the above-mentioned reactive derivatives of the compounds of general formula (III) are used, then the reaction is preferably carried out in the presence of an inorganic or tertiary organic base which is useful for binding the acid liberated in the reaction; however, an excess of the compound of general formula (III) can also be used as an acid binding agent. This reaction can be performed in an inert organic solvent or without any solvent.

When both X and Y are hydroxyl groups, then the condensation is preferably accomplished in the presence of inorganic or organic acids or their acidic salts commonly used for promoting the ether formation, under atmospheric or reduced pressure whilst the water formed is azeotropically distilled out. Useful solvents are e.g.: aromatic or aliphatic hydrocarbons such as n-heptane, toluene, xylene; as well as aliphatic or alicyclic ethers such as di(n-butyl)ether, dioxane and the like.

According to process (b) of the invention, a benzhydryl halide of the general formula (IX), preferably a chloride or bromide, is reacted with a piperazine derivative of the general formula (V), wherein the meanings of the substituents are as defined above, under conditions described for process (a). After completion of the reaction the product is isolated. The reaction mixture may be worked up e.g. in such a way that the mixture is poured into water and the product is separated by solvent extraction. The organic phase is washed with water until free of halogen, dried and evaporated. The thus-obtained crude product is purified e.g. by chromatography and/or recrystallization.

According to process (c) of the invention, a reactive derivative, preferably the mesylate, tosylate, bromide or chloride of a compound of the general formula (VI), wherein the meanings of the substituents are as defined above, is reacted with an 1-alkyl-, 1-alkenyl-or 1-alkynylpiperazine derivative of the general formula (VII), wherein $R_6$ is as defined above. This reaction is preferably carried out in an organic solvent, in the presence of a base useful for binding the acid liberated in the reaction. Suitable solvents for this reaction are e.g.: hydrocarbons such as ligroin, benzene, toluene or xylene; halogenated hydrocarbons such as chloroform; ethers such as dioxane; alcohols such as ethanol; esters such as ethyl acetate; acid amides such as dimethylformamide; ketones such as acetone and methyl isobutyl ketone; or the mixtures of the above solvents. As acid binding agents inorganic or tertiary organic bases can be used, e.g. alkali metal carbonates and hydroxides, triethylamine, pyridine and the like or an excess of the piperazine derivative of the general formula (VII). An excess of the last one can also be used as solvent. The reaction may be accomplished at a temperature between 20° C. and the boiling point of the solvent, optionally in the presence of a catalyst. Useful catalysts are e.g. the alkali metal iodides.

On carrying out process (d) of the invention, an 1-benzhydryloxyalkylpiperazine is reacted with a compound of the general formula (IX), preferably under similar conditions as defined above for process (c).

According to process (e) of the invention, a compound of the general formula (VIII), wherein $R_1$, $R_2$, $R_3$, $R_4$, $R_5$ and n are as defined above, is brought into reaction with an aldehyde of the general formula (X), wherein $R_7$ stands for a $C_{2-5}$ alkyl, alkenyl or alkynyl group, in the presence of a suitable reducing agent. This reaction is preferably carried out in an inert organic solvent, by using e.g. hydrogen as reducing agent, in the presence of a catalyst commonly used for catalytic hydrogenation, such as Raney nickel. According to a particularly preferable embodiment, this reaction is accomplished in the presence of an alkali metal cyanoborohydride, preferably sodium cyanoborohydride [C. F. Lane: Synthesis, 1975, 135].

According to a preferable embodiment of process (f) of the invention, a piperazine derivative of the general formula (VIII), wherein $R_1$, $R_2$, $R_3$, $R_4$, $R_5$ and n are as defined above, is reacted with a reactive derivative such as the chloride, anhydride or the like of a $C_{3-6}$ alkane-, alkene- or alkynecarboxylic acid in an inert solvent, e.g. toluene or chloroform, in the presence of an acid binding agent such as triethylamine, then, if desired, the thus-obtained acid amide of the general formula (I), wherein $R_6$ stands for a

group and $R_7$ is as defined above, is reduced to a compound of the general formula (I), wherein $R_6$ represents a $C_{3-6}$ alkyl, alkenyl or alkynyl group. This reduction is carried out by using e.g. lithium aluminium hydride in an inert organic solvent such as aliphatic or cycloaliphatic ethers, e.g. ethyl ether, tetrahydrofuran or a mixture thereof, under an inert gas such as nitrogen or argon, whereafter the complex formed is hydrolyzed.

According to process (g) of the invention, a novel compound of the general formula (I), wherein $R_1$, $R_2$, $R_3$, $R_4$, $R_5$ and n are as defined above and $R_6$ means a $C_{3-6}$ alkynyl group, may be transformed, if desired, to an other new compound of the general formula (I), namely to the corresponding alkenyl or alkyl derivative through partial or complete reduction of the triple bond. When this reduction is continued up to the absorption of one mole of hydrogen, e.g. in the presence of a catalyst useful for the partial saturation of the triple bond, then novel compounds of the general formula (I) are obtained, wherein $R_6$ is an alkenyl group. Useful catalysts for this purpose are e.g.: Raney nickel catalyst poisoned by zinc acetate and used in the presence of piperdine; or Lindlar's catalyst (Pd(CaCO$_3$)PbO) in the presence of quinoline. On carrying out the reduction up to the complete saturation of the triple bond, compounds of the general formula (I) are obtained, wherein $R_6$ stands for an alkyl group. This reduction is preferably accomplished by catalytic hydrogenation. Suitable catalysts for this hydrogenation are e.g.: metals such as ruthenium, palladium, platinum, nickel, iron, copper, cobalt, chrom, zinc, molybdenum, tungsten and the like; or the oxides and sulfides of these metals. The catalytic hydrogenation may also be carried out in the presence of catalysts previously precipitated onto the surface of a carrier. Useful carriers are e.g. carbon, silicon dioxide, aluminium oxide as well as the carbonates and sulfates of the alkali earth metals. Suitably, the reduction is performed by hydrogenation in the presence of a palladium, platinum or Raney nickel catalyst in a solvent inert to the reaction. Useful solvents are e.g.: lower aliphatic alcohols, ethers, esters as well as aliphatic, cycloaliphatic and aromatic hydrocarbons or the mixtures of these solvents. The hydrogenation can be carried out under atmospheric or higher pressure, at a temperature between 20° C. and the boiling point of the reaction mixture. The reduction is continued until the calculated amount of hydrogen is taken up, then the catalyst is filtered, the filtrate is evaporated and the thus-obtained product is purified by distillation and/or recrystallization.

According to process (h) of the invention, a novel compound of the general formula (I), wherein $R_1$, $R_2$, $R_3$, $R_4$, $R_5$ and n are as defined above and $R_6$ stands for a $C_{3-6}$ alkenyl group, is reduced to the corresponding compound of the general formula (I), wherein $R_6$ is an alkyl group, by using catalytic hydrogenation described in process (g).

According to process (i) of the invention, an acid amide of the general formula (XI), wherein $R_1$, $R_2$, $R_3$, $R_4$, $R_5$, $R_6$ and n are as defined above, is reduced as described in process (f) of the invention.

If desired, the compounds of the general formula (I) can be transformed to their pharmaceutically acceptable acid addition salts or quaternary ammonium salts in a known way. For the preparation of acid addition salts, inorganic and organic acids can be used, e.g.: hydrogen halides, such as hydrogen chloride, hydrogen bromide and the like; sulfuric acid and phosphoric acid; formic, acetic, propionic, oxalic, glycolic, maleic, fumaric, succinic, tartaric, ascorbic, citric, malic, salicylic, benzoic, cinnamic, aspartic, glutamic, N-acetylaspartic or N-acetylglutamic acid; as well as alkanesulfonic acids such as methanesulfonic acid and arenesulfonic acids such as p-toluenesulfonic acid and the like.

The acid addition salts can be prepared e.g. in such a way that the appropriate acid is added to a solution containing the compound of the general formula (I) in an inert solvent, e.g. to the ethanolic solution thereof, then the thus-obtained salt is precipitated by adding preferably a water-immiscible organic solvent such as ethyl ether.

For preparation of the quaternary salts, a lower alkyl, alkenyl or benzyl halide or an alkyl sulfate may preferably be used. The quaternization is carried out in an organic solvent, suitably e.g. in acetone, acetonitrile, ethanol or a mixture thereof at a temperature between room temperature and the boiling point of the solvent. The thus-formed quaternary salt is isolated e.g. by filtration and, if desired, purified by recrystallization.

The compounds of the invention are transformed to pharmaceutical compositions. These compositions can be administered through oral, rectal and/or parenteral route. For oral administration, the composition can be prepared in the form of tablets, dragées or capsules. For the preparation of oral compositions, e.g. lactose or starch can be used as vehicle. Suitable binding or granulating agents are e.g. gelatine, sodium carboxymethylcellulose, methylcellulose, polyvinylpyrrolidone or starch gum. As disintegrating agents, particularly potato starch or microcrystalline cellulose can be added, but ultraamylopectin or formaldehyde-casein is also useful. Talc, colloidal silicic acid, stearin as well as calcium and magnesium stearate or the like can be used as anti-adhesive and sliding agents.

Tablets can be prepared e.g. by wet granulation and subsequent compression. The mixture containing the active ingredients and vehicles and optionally a part of the disintegrating agent is granulated together with an aqueous, ethanolic or aqueous-ethanolic solution of the binding agents in an appropriate equipment, then the granulate is dried. Thereafter, the other disintegrating, sliding and anti-adhesive additives are mixed to the dried granulate and the mixture is compressed to tablets. Optionally the tablet is provided with a dissecting groove. The tablets can also be prepared by the direct compression of the mixture containing the active ingredient together with the needed additives. If desired, the tablets may be transformed to dragées by using the protective, flavouring and dyeing agents such as sugar, cellulose derivatives (methyl- or ethylcellulose or sodium carboxymethylcellulose), polyvinylpyrrolidone, calcium phosphate, calcium carbonate, food dyes, aromatizing agents, iron oxide pigments and the like which are commonly used in the pharmaceutical industry. For the preparation of capsules, the mixture of the active ingredients with the additives is filled into a capsule.

For rectal administration, the composition is prepared in the form of a suppository. In addition to the active ingredient, the suppository also contains a vehicle base material, the so-called "adeps pro suppositorio" (fat for suppository). As vehicles, vegetable fats such as hardened vegetable oils and the triglycerides of $C_{12-18}$ fatty acids, preferably vehicles with the trade mark Witepsol®, can be used. The active ingredient is homogeneously dispersed in the molten vehicle mass and then the suppositories are prepared by moulding.

For parenteral administration, the composition is prepared in the form of an injectable solution. For the preparation of injectable solutions, the active ingredients are dissolved in distilled water and/or various organic solvents, e.g. glycol ethers, optionally in the presence of solubilizing agents such as polyoxyethylene sorbitan monolaurate, monooleate or monostearate (Tween 20, Tween 60 and Tween 80, respectively). In addition, the injectable solution also contains various additives such as preservatives, e.g. benzyl alcohol, methyl or propyl 4-hydroxybenzoate, benzalkonium chloride, phenylmercury borate and the like; as well as antitoxidants, e.g. ascorbic acid, tocopherol, sodium pyrosulfate and optionally complex forming agents such as an ethylenediamine tetraacetate salt for binding the metal traces, as well as buffers for adjusting the pH value and optionally a local anaesthetizing agent, e.g. lidocaine. The injectable solution containing the active ingredient of the invention is filtered before filling into the ampoule and sterilized after filling.

The daily doses depend upon the condition of the patient and the disease to be treated and are in general between 5 and 200 mg for adults in the case of an oral administration.

The invention also relates to a method for treating diseases arising from a decrease in the dopamine level, i.e. from the hypofunction of the dopaminergic system. This process comprises the use of a therapeutically effective amount of an 1,4-disubstituted piperazine derivative of the general formula (I) or a pharmaceutically acceptable acid addition or quaternary ammonium salt thereof to a subject in need of such treatment.

The invention is illustrated in detail by the aid of the following non-limiting Examples.

EXAMPLE 1

Preparation of
1-[2-[bis(4-fluorophenyl)-methoxy]ethyl]-4-(2-propenyl)piperazine dihydrochloride A suspension containing 2.4 g of 50% sodium hydride (oily dispersion) and 11.0 g of 4,4'-difluorobenzyhdrol in 60 ml of anhydrous toluene is refluxed under argon for 15 minutes in an argon atmosphere, then a solution of 9.4 g of 1-(2-chloroethyl)-4-(2-propenyl)piperazine in 70 ml of anhydrous toluene is portionwise added. The mixture is refluxed for additional 2 hours, then cooled down and 40 ml of water are added. The organic layer is separated, washed to chloride-free with water, dried over anhydrous sodium sulfate and evaporated under reduced pressure. The residue is purified on a Kieselgel column by using a benzene-methanol mixture as eluant. The appropriate fractions are evaporated, the residue is dissolved in anhydrous isopropanol and the aimed salt is precipitated by adding ethereal hydrogen chloride solution. The dihydrochloride melts at 189°–191° C.

Analysis: Calculated for $C_{22}H_{26}F_2N_2O$ (base): C 70.94; H 7.04; F 10.20; N 7.52%; found: C 70.77; H 7.11; F 10.40; N 7.63%.

EXAMPLE 2

Preparation of
1-[2-[(4-chlorophenyl)-(4-fluorophenyl)methoxy]ethyl]-4-(2-propenyl)-piperazine dihydrochloride A mixture containing 18.0 g of 2-[(4-chlorophenyl)-(4-fluorophenyl)methoxy]ethyl chloride, 6.3 g of 1-allylpiperazine, 8.3 g of powdered anhydrous potassium carbonate and 0.83 g of potassium iodide in 170 ml of methyl isobutyl ketone is refluxed under stirring for 15 hours. After cooling down, the reaction mixture is evaporated under reduced pressure. Water is added to the reaction mixture which is then extracted with benzene. The organic phase is washed with water, dried over anhydrous sodium sulfate and, after evaporation, the residue is taken up in anhydrous ether. The ethereal solution is treated with ethereal hydrogen chloride solution, the precipitated salt is filtered and dried to give the aimed dihydrochloride, m.p.: 199°–200° C.

Analysis: Calculated for $C_{22}H_{26}ClFN_2O$ (base): C 67.94; H 6.74; Cl 9.12; N 7.20; F 4.89%; found: C 68.10; H 6.53; Cl 9.30; N 7.08; F 5.10%.

The following compounds are prepared analogously to the process described in the above Example.

(a) 1-[2-[(2-Chlorophenyl)-(4-fluorophenyl)-methoxy]ethyl]-4-propylpiperazine dihydrochloride, m.p.; 213°–214° C., is prepared by reacting 1-chloro-2-[(2-hydroxyethoxy)-(4-fluorophenyl)-methyl]benzene methanesulfonate with 1-propyl-piperazine.

Analysis: Calculated for $C_{22}H_{28}ClFN_2O$ (base): C 67.59; H 7.22; Cl 9.07; F 4.86; N 7.17%; found: C 67.66; H 7.38; Cl 9.24; F 5.03; N 7.40%.

(b) 1-[3-(Diphenylmethoxy)propyl]-4-propylpiperazine, b. p. 185°–188° C./0.01 Hgmm, is prepared by reacting 1-[(3-hydroxypropoxy)phenylmethyl]benzene p-toluenesulfonte with 1-propylpiperazine.

Analysis: Calculated for $C_{23}H_{32}N_2O$ (base): C 78.36; H 9.15; N 7.95; found: C 78.41; H 9.30; N 8.07%.

(c) 1-[2-[3-Nitro-4-[4-(2-propenyl)piperazine-1-yl-phenyl]-phenylmethoxy]ethyl]-4-(2-propenyl)-piperazine tetramaleate, m.p.: 109°–112° C., is prepared by reacting 2-[(4-chloro-3-nitrophenyl)-phenylmethoxy]ethyl chloride with 1-(2-propenyl)piperazine.

Analysis: Calculated for $C_{29}H_{39}N_5O_3$(base): C 68.88; H 7.77; N 13.85%; found: C 68.67; H 7.84; N 13.97%.

(d) 1-[2-[(4-Chlorophenyl)-(4-fluorophenyl)methoxy]ethyl]-4-(2-propynyl)piperazine dihydrochloride, m.p.: 186°–188° C., is prepared by reacting 2-[(4-chlorophenyl)-(4-fluorophenyl)methoxy]ethyl chloride with 1-(2-propynyl)piperazine.

Analysis: Calculated for $C_{22}H_{24}ClFN_2O$ (base): C 68.29; H 6.25; Cl 9.16; F 4.91; N 7.24%; found: C 68.47; H 6.38; Cl 9.00; F 4.77; N 7.32%.

(e) 1-[2-[(3,4-Dichlorophenyl)phenylmethoxy]ethyl]-4-(2-propynyl)piperazine dihydrochloride, m.p.: 201°–203° C., is prepared by reacting 2-[(3,4-dichlorophenyl)phenylmethoxy]ethyl bromide with 1-(2-propynyl)piperazine.

Analysis: Calculated for $C_{22}H_{24}Cl_2N_2O$ (base): C 65.71; H 6.00; Cl 17.58; N 6.95%; found: C 65.60; H 6.11; Cl 17.33; N 7.13%.

(f) 1-[2-[(4-Bromophenyl)-(4-fluorophenyl)methoxy]-ethyl]-4-(2-propynyl)piperazine dihidrochloride, m.p.: 179°–181° C., is prepared by reacting 2-[(4-bromophenyl)-(4-fluorophenyl)-methoxy]ethyl bromide with 1-(2-propynyl)piperazine.

Analysis: Calculated for $C_{22}H_{24}BrFN_2O$ (base): C 61.26; H 5.61; Br 18.53; F 4.40; N 6.49%; found: C 61.17; H 5.83; Br 18.44; F 4.61; N 6.40%.

(g) 1-[2-[(4-Fluorophenyl)-phenylmethoxy]ethyl]-4-(2-propynyl)piperazine dihychloride, m.p.: 186°–187° C., is prepared by reacting 2-[(4-fluorophenyl)-phenyl-methoxy]ethyl chloride with 1-(2-propenyl)piperazine.

Analysis: Calculated for $C_{22}H_{25}FN_2O$ (base): C 74.97; H 7.15; F 5.39; N 7.95%; found: C 75.21; H 7.34; F 5.55; N 7.79%.

(h) 1-[2-[bis(4-Chlorophenyl)methoxy]ethyl]-4-(2-propynyl)piperazine dihydrochloride, m.p.: 194°–196° C., is prepared by reacting 2-[bis(4-chlorophenyl)methoxy]ethyl tosylate with 1-(2-propynyl)-piperazine.

Analysis: Calculated for $C_{22}H_{24}Cl_2N_2O$ (base): C 65.51; H 6.00; Cl 17.58;˙N 6.95%; found: C 65.69; H 5.87; Cl 17.45; N 6.84%.

EXAMPLE 3

Preparation of
1-[2-[1-(2,5-dimethylphenyl)-1-phenylpropoxy]ethyl]-4-(2-propenyl)piperazine dihydrogen fumarate To a mixture containing 10.6 g of 1-[2-[1-(2,5-dimethylphenyl)-1-phenylpropoxy]ethyl]piperazine and 4.6 g of anhydrous, powdered potassium carbonate in 90 ml of anhydrous benzene, 3.6 g of allyl bromide dissolved in 10 ml of benzene are dropped while mild refluxing, then the reaction mixture is boiled for one additional hour. After cooling down, water is added to the mixture, the organic phase is separated, washed with water until neutral, dried over anhydrous sodium sulfate and evaporated under reduced pressure. The anhydrous ethanolic solution of the evaporation residue is treated with an ethanolic fumaric acid solution. The solid precipitate is recrystallized from methanol to give the aimed dihydrogen fumarate, m.p. 202°–204° C.

Analysis: Calculated for $C_{26}H_{36}N_2O$ (base): C 79.54; H 9.24; N 7.14%; found: C 79.31; H 9.28; N 7.30%.

EXAMPLE 4

Preparation of
1-[2-[bis(4-fluorophenyl)-methoxy]ethyl]-4-hexylpiperazine dihydrochloride To a solution containing 2.3 g of lithium aluminium hydride in 60 ml of anhydrous ether, 21.5 g of 1-[2-[bis(4-fluorophenyl)methoxy]ethyl]-4-(1-oxohexyl)-piperazine dissolved in 100 ml of anhydrous ether are portionwise added under argon gas while stirring. The reaction mixture is refluxed for one additional hour, then cooled to 0° C., and decomposed by adding aqueous sodium hydroxide solution. The precipitate is filtered and washed with ether. The combined ethereal phase is washed with water, dried over anhydrous magnesium sulfate and evaporated. The residue is dissolved in ethanol and the aimed salt is precipitated by adding ethereal hydrogen chloride solution, m.p.: 212°–213° C.

Analysis: Calculated for $C_{25}H_{34}F_2N_2O$ (base): C 72.08; H8.23; F 9.12; N 6.73%; found: C 72.20; H 8.28; F 9.18; N 6.70%.

EXAMPLE 5

Preparation of
1-[2-[bis(4-fluorophenyl)-methoxy]ethyl]-4-(1-oxo-propyl)piperazine hydrochloride 2.3 g of propionyl chloride dissolved in 10 ml of 1,2-dichloroethane are dropped to a solution containing 8.3 g of 1-[2-[bis(4-fluorophenyl)methoxy]-ethyl]piperazine and 4.2 ml of triethylamine in 80 ml of 1,2-dichloroethane, whereupon the mixture is stirred for additional 30 minutes. Then, water is added to the reaction mixture, after separation the organic layer is washed with water, dried over anhydrous magnesium sulfate and evaporated under reduced pressure. The residue is dissolved in ethanol, after adding ethereal hydrogen chloride solution the precipitated salt is filtered and recrystallized from ethanol to give the aimed hydrochloride, m.p.: 191°–192° C.

The following compounds were analogously prepared from the appropriate starting materials:

(a) 1-[2-(diphenylmethoxy)ethyl]-4-(1-oxo-2-propenyl)-piperazine hydrochloride, m.p.: 189°–190 ° C.;

(b) 1-[2-(diphenylmethoxy)ethyl]-4-(1-oxobutyl)-piperazine hydrochloride, m.p.: 192°–193° C.;

(c) 1-[2-(diphenylmethoxy)ethyl]-4-(1-oxopentyl)-piperazine hydrochloride, m.p.: 180.5°–181.5° C.;

(d) 1-[2-(dephenylmethoxy)ethyl]-4-(1-oxohexyl)-piperazine hydrochloride, m.p.: 187°–190° C.;

(f) 1-[2-[bis(4-fluorophenyl)methoxy]ethyl]-4-(1-oxohexyl)piperazine hydrochloride, m.p.: 169°–170° C.

By reducing the above acid amide-type compounds of the general formula (I) according to Example 4, the further appropriate compounds of the general formula (I) can be obtained.

(g) 1-[2-(Diphenylmethoxy)ethyl]-4-(n-hexyl)-piperazine dihydrochloride, m.p.: 216°–217° C.

Analysis: Calculated for $C_{25}H_{36}N_2O$ (base): C 78.90; H 9.54; N 7.36%; found: C 78.78; H 9.66; N 7.30%.

(h) 1-[2-(Diphenylmethoxy)ethyl]-4-(n-pentyl)-piperazine dihydrochloride, m.p.: 213°–214° C.

Analysis: Calculated for $C_{24}H_{34}N_2O$ (base): C 78.64; H 9.35; N 4.37%; found: C 78.60; H 9.48; N 4.39%.

(i) 1-[2-(Diphenylmethoxy)ethyl]-4-(n-butyl)-piperazine dihydrochloride, m.p.: 209°–211° C.

Analysis: Calculated for $C_{23}H_{32}N_2O$ (base): C 78.36; H 9.15; N 7.95%; found: C 78.17; H 9.20; N 7.84%.

(j) 1-[2-[bis(4-Fluorophenyl)methoxy]ethyl]-4-n-propyl)piperazane dihydrochloride, the physical characteristics of which are the same as given in Example 7.

(k) 1-[2-(Diphenylmethoxy)ethyl]-4-(2-propenyl)-piperazine dihydrochloride, the physical characteristics of which are the same as given in Example 13.

EXAMPLE 6

Preparation of 1-8
2-[(4-hydroxyphenyl)-4-(4-fluorophenyl)methoxy]e-thyl]-4-propyl-piperazine di(hydrogen maleate)

A solution containing 13.3 g of 1-[2-[(4 -benzyloxyphenyl)---(4-fluorophenyl)methoxy]ethyl]-4-(2-propenyl)piperazine dihydrochloride in 140 ml of methanol is hydrogented under atmospheric pressure in the presence of 6.0 g 10% palladium-on-charcoal. After completion of the reaction, the catalyst is filtered and the filtrate is evaporated under reduced pressure. The residue is dissolved in water, the base is liberated by adding aqueous ammonium hydroxide solution and extracted into ether. The ethereal layer is extracted with water, dried over anhydrous magnesium sulfate and the ethereal phase is treated with an ethereal maleic acid solution. The precipitate is filtered and dried to give the aimed maleate salt, m.p.: 129°–132° C.

Analysis: Calculated for $C_{22}H_{29}FN_2O_2$(base): C 70.94; H 7.85; F 5.10; N 7.52%; found: C 71.10; H 7.64; F 5.28; N 7.39%.

EXAMPLE 7

Preparation of 1-[2-[(bis(4-fluorophenyl)-methoxy]ethyl]-4-propylpiperazine dihydrochloride A mixture containing 2 g of 1-[2-[bis(4-fluorophenyl)-methoxy]ethyl]piperazine, 0.35 g of propionaldehyde and 0.4 g of sodium cyanoborohydride in 28 ml of methanol is stirred at room temperature for 4 hours, then 35 ml of 0.4N hydrochloric acid solution are added and the mixture is stirred at room temperature for additional one hour. After distilling off the methanol under reduced pressure, the residue is alkalized by adding aqueous sodium hydroxide solution and extracted with benzene. The benzene layer is washed with water, dried over anhydrous magnesium sulfate and evaporated under reduced pressure. The residue is taken up in anhydrous ethanol, then ethereal hydrogen chloride solution is added to give the aimed product, m.p.: 199°–200° C.

Analysis: Calculated for $C_{22}H_{28}F_2N_2O$ (base): C 70.56; H 7.54; F 10.5; N 7.48; found: C 70.67; H 7.48; F 10.19; N 7.67%.

EXAMPLE 8

Preparation of 1-[2-[1-bis(4-fluorophenyl)-ethoxy]ethyl]-4-(2-propenyl)piperazine dihydrochloride 4.6 g of 4'-fluoroacetophenone dissolved in 10 ml of tetrahydrofuran are dropped to a solution containing 20.0 ml of 1.5M 4-fluorophenylmagnesium bromide in tetrahydrofuran. The mixture is refluxed for additional one hour, then cooled to room temperature and, after adding a solution containing 5.7 g of 1-(2-chloroethyl)-4-(2-propenyl)piperazine in 45 ml of anhydrous xylene, the mixture is boiled for additional 3 hours. After cooling down, the mixture is poured into water, the organic layer is separated and the aqueous phase is extracted twice with 25 ml of xylene each. The aqueous acidic solution is alkalized by adding ammonium hydroxide solution and extracted with ether. The combined ethereal phase is dried over anhydrous magnesium sulfate and evaporated. The residue is chromatographed on a Kieselgel column by using a 98:2 mixture of chloroform with methanol as eluant. The appropriate fractions are combined, evaporated under pressure and the dihydrochloride salt is precipitated by adding an ethereal hydrogen chloride solution. After filtering and drying the crystals, the aimed product is obtained with a m.p. of 187°–189.5° C.

Analysis: Calculated for $C_{23}H_{28}F_2N_2O$ (base): C 71.47; H 7.30; F 9.83; N 7.25%; found: C 71.60; H 7.37; F 9.75; N 7.30%.

EXAMPLE 9

Preparation of 1-[2-[bis(4-chlorophenyl)-methoxy]ethyl]-4-(2-propenyl)piperazine dihydrochloride After reacting 8.5 g of 4-(2-hydroxyethyl)-1-(2-propenyl)-piperazine in 30 ml of methanol with 2.7 sodium methoxide, the methanol is distilled off from the reaction mixture. After adding 100 ml of toluene to the residue, the mixture is made free from the traces of methanol by azeotropic distillation (about 20 ml of toluene are distilled off). To the residue, a solution containing 14.1 g of 4,4'-dichlorobenzhydryl chloride in 30 ml of anhydrous toluene is dropped, the mixture is boiled under reflux for 4 hours, then cooled down and water is added. The organic phase is separated, washed with water, dried over anhydrous magnesium sulfate and evaporated under reduced pressure. The residue is taken up in anhydrous ether, then etheral hydrogen chloride solution is added. The precipitate is filtered and recrystallized from a mixture of methanol and ether to give the aimed dihydrochloride, m.p.: 218.5°–220° C.

Analysis: Calculated for $C_{22}H_{26}Cl_2N_2O$ (base): C 65.18; H 6.47; Cl 17.49; N 6.91%; found: C 65.31; H 6.52; Cl 17.29; N 6.83%.

EXAMPLE 10

Preparation of 1-[2-[(4-fluorophenyl)-phenyl-methoxy]ethyl]-4-propyl-piperazine dihydrochloride A mixture containing 11.0 g of 4-fluorobenzhydryl chloride and 17.2 g of 1-(2-hydroxyethyl)-4-propylpiperazine is heated at 160° to 170° C. under nitrogen for 30 minutes. Thereafter, the mixture is cooled down to 90° to 100° C. and water is added. After cooling to room temperature, the mixture is extracted with benzene, the organic phase is washed with water until neutral, dried over anhydrous magnesium sulfate and evaporated. After dissolving the residue in anhydrous ethanol, the dihydrochloride of the base is formed by adding ethereal hydrogen chloride solution. The mixture is diluted with ether and the precipitated crystalline dihydrochloride is filtered, washed with ether and dried, m.p.: 194°–195° C.

Analysis: Calculated for $C_{22}H_{29}FN_2O$ (base): C 74.12; H 8.20; F 5.33; N 7.86%; found: C 74.30; H 8.33; F 5.41; N 7.89%.

The following compounds, wherein $R_5$ stands for hydrogen, n is 2 and $R_6$ means 2-propenyl, are prepared analogously to the process described in Example 9 or 10 from the appropriate starting materials.

| | $R_1$ | $R_2$ | $R_3$ | $R_4$ | Salt | M.p.: °C. |
|---|---|---|---|---|---|---|
| (b) | H | 2-Cl | H | 4-F | 2HCl | 207–209 |
| (c) | 4-CF$_3$ | H | H | 4-F | 2HCl | 198–200 |
| (d) | 4-Cl | 3-Cl | H | H | 2HCl | 200–202 |
| (e) | 4-F | H | 3-C$_2$H$_5$O | 4-OH | 2HCl | 156–158 |
| (f) | H | 3-CF$_3$ | H | 4-F | 2HCl | 192–193 |
| (g) | H | 2-CH$_3$ | H | 4-F | 2HCl | 199–201 |
| (h) | 4-F | H | 4-benzyloxy | H | dimaleate | 172–174 |
| (i) | 4-Br | H | H | 4-F | 2HCl | 197–198.5 |
| (j) | H | H | 3-CF$_3$ | H | dimaleate | 171–172 |

EXAMPLE 11

Preparation of
1-[(2-[4-chlorophenyl)-(4-fluorophenyl)methoxy]ethyl]-
4-propylpiperazine dihydrochloride A solution containing 8.1 g of 1-[(2-[4-chlorophenyl)-(4-fluorophenyl)methoxy]acetyl]-4-propylpiperazine in 100 ml of ether is dropped to 30 ml of 1.0M ethereal lithium aluminium hydride solution under nitrogren gas while stirring, then the mixture is refluxed for 3 hours. Thereafter, the mixture is cooled down to 0° C. and decomposed by adding aqueous sodium potassium tartrate solution. The aqueous phase is extracted with ether, the combined etheral solution is washed with saturated aqueous sodium chloride solution, dried over anhydrous magnesium sulfate and evaporated. To the ethanolic solution of the residue, ethereal hydrogen chloride solution is added up to a pH value of 2.5 to 3. The precipitated crystals are filtered and dried to give the aimed dihydrochloride, m.p.: 195°–197° C.

Analysis: Calculated for $C_{22}H_{28}ClFN_2O$ (base): C 67.59; H 7.22; Cl 9.07; F 4.86; N 7.17%; found: C 67.71; H 7.40; Cl 9.18; F 4.82; N 7.30%.

EXAMPLE 12

(a) Preparation of
1-[2-[bis(4-fluorophenyl)methoxy]ethyl]-4-(2-methyl-2-propenyl)-piperazine dihydrochloride A mixture containing 6.6 g of 1-[2-[bis(4-fluorophenyl)methoxy]ethyl]piperazine, 3.0 g of powdered anydrous potassium carbonate, 2.0 g of 3-chloro-2-methylpropene and 70 ml of anhydrous acetone is refluxed under stirring for 6 hours, then the acetone is distilled off under reduced pressure. The residue is taken up in water and extracted with benzene. The organic phase is washed with water, dried over anhydrous potassium carbonate and evaporated under reduced pressure. The residue is purified by chromatography on a Kieselgel column with chloroform as eluant. After evaporating the appropriate fractions, the aimed dihydrochloride is precipitated by adding ethereal hydrogen chloride solution, m.p.: 197°–199° C.

The base is liberated from the dihydrochloride by adding dilute aqueous ammonium hydroxide solution.

Analysis: Calculated for $C_{23}H_{28}F_2N_2O$ (base): C 71.48; H 7.30; F 9.83; N 7.25; found: C 71.60; H 7.35; F 9.74; N 7.33%.

The following compounds are prepared analogously to the process described in the above Example.

(b)
1-[2-[bis(4-Fluorophenyl)methoxy]ethyl]-4-(n-butyl)-piperazine dihydrochloride, m.p.: 219°–220° C.

Analysis: Calculated for $C_{23}H_{30}F_2N_2O$ (base): C 71.10; H 7.78; F 9.78; N 7.21%; found: C 71.23; H 7.81; F 9.63; N 7.33%.

(c)
1-[2-(4-Chlorophenyl)-4-(4-fluorophenyl)methoxy]ethyl]-4-(n-butyl)piperazine dihydrochloride, m.p.: 220°–221° C.

Analysis: Calculated for $C_{23}H_{30}ClFN_2O$ (base): C 68.21; H 7.47; Cl 8.76; F 4.69; N 6.92%; found: C 68.00; H 7.41; Cl 8.53; F 4.81; N 7.03; %.

(d)
1-[2-[(3,4-Dichlorophenyl)-phenylmethoxy]ethyl]-4-(n-butyl)piperazine dihydrochloride, m.p.: 221°–222.5° C.

Analysis: Calculated for $C_{23}H_{30}Cl_2N_2O$ (base): C 65.55; H 7.18; Cl 16.83; N 6.65%; found: C 65.73; H 7.24; Cl 16.66; N 6.79%.

EXAMPLE 13

Preparation of
1-[2-(diphenylmethoxy)ethyl]-4-(2-propenyl)-piperazine dihydrochloride A solution containing 16.7 g of 1-[2-(diphenylmethoxy)-ethyl]-4-(2-propynyl)piperazine, 0.4 g of zinc acetate dihydrate and 10 ml of piperidine in 170 ml of methanol is hydrogenated in the presence of 3.0 g of Raney nickel catalyst under atmospheric pressure. After absorption of the calculated amount of hydrogen, the catalyst is filtered and the filtrate is evaporated under reduced pressure. The residue is taken up in benzene, washed with water, dried over anhydrous magnesium sulfate and evaporated. The residue is purified by Kieselgel column chromatography by using a 98:2 mixture of chloroform and methanol as eluant. From the appropriate fraction, the aimed dihydrochloride is obtained by adding an ethereal hydrogen chloride solution, m.p.: 204°–206° C.

Analysis: Calculated for $C_{22}H_{28}N_2O$ (base): C 78.53; H 8.39; N 8.33%; found: C 78.67; H 8.29; N 8.35%.

EXAMPLE 14

Preparation of
1-[2-[bis(4-fluorophenyl)-methoxy]ethyl]-4-(2-propynyl)piperazine dihydrochloride A mixture containing 33.2 g of 1-[2-[bis(4-fluorophenyl)methoxy]ethyl]piperazine, 15.5 g of anhydrous powdered potassium carbonate, 13.1 g of a 30% weight toluenic propargyl bromide solution and 330 ml of anhydrous acetone is stirred at room temperature for one hour, then evaporated under reduced pressure. The residue is taken up with water and extracted with benzene. The organic layer is washed with water, dried over anhydrous sodium sulfate and evaporated under reduced pressure. The residue is purified by chromatography on a Kieselgel column by using chloroform as eluant. The aimed dihydrochloride, m.p.: 187°–188° C., is precipitated by adding ethereal hydrogen chloride solution to an ethereal solution of the base.

Analysis: Calculated for $C_{22}H_{24}F_2N_2O$ (base): C 71.33; H 6.53; F 10.26; N 7.56%; found: C 71.41; H 6.47; F 10.12; N 7.58%.

The following compounds are prepared from the appropriate starting materials analogously to the process described in the above Example.

(a)
1-[2-(Diphenylmethoxy)ethyl]-4-(2-propynyl)-piperazine dihydrochloride, m.p.: 205°–206° C.

Analysis: Calculated for $C_{22}H_{26}N_2O$ (base): C 79.00; H 7.84; N 8.38%; found: C 79.20; H 7.78; N 8.19%.

(b) 1-[2-[(4-trifluoromethylphenyl)-(4-fluorophenyl)methoxy]ethyl]-4-(2-propynyl)piperazine, oily substance Analysis: Calculated for $C_{23}H_{24}F_4N_2O$ (base): C 65.70; H 5.75; F 18.08; N 6.66%; found: C 65.86; H 5.76; F 18.20; H 6.51%.

EXAMPLE 15

Preparation of 1-[2-[(4-trifluoromethylphenyl)-(4-fluorophenyl)methoxy]ethyl]-4-(n-propyl)-piperazine dihydrochloride A solution containing 4.2 g of 1-[2-[(4-trifluoromethylphenyl)-4-fluorophenyl)methoxy]ethyl]-4-(2-propynyl)piperazine in 45 ml of methanol is hydrogenated in the presence of 0.4 g of 10% palladium-on-charcoal under atmospheric pressure until the calculated amount of hydrogen is absorbed. After filtering the catalyst, the solution is evaporated. The residue is dissolved in benzene, the organic layer is washed with water, dried over anhydrous sodium sulfate and evaporated. The residue is dissolved in ethanol and ethereal hydrogen chloride is added until reaching a pH value of 2.5 to 3. The crystalline precipitate is filtered and recrystallized from methanol to give the aimed dihydrochloride, m.p.: 212°–214° C.

Analysis: Calculated for $C_{23}H_{28}F_4N_2O$ (base): C 65.08; H 6.65; F 17.90; N 6.60%; found: C 65.10; H 6.69; F 17.81; N 6.63%.

EXAMPLE 16

Preparation of 1-[2-[(4-fluorophenyl)-phenyl-methoxy]ethyl]-4-(2-propenyl)-piperazine dihydrochloride 12.0 g of 4-toluenesulfonic acid monohydrate and 5.1 g of 1-(2-hydroxyethyl)-4-(2-propenyl)piperazine dissolved in 45 ml of dimethylformamide are added to a solution containing 7.9 g of 4-fluorobenzhydrol in 150 ml of toluene, whereupon the mixture is boiled and the water formed in the condensation reaction is azeotropically distilled off. After completion of the reaction (which is controlled by thin layer chromatography), the mixture is cooled and extracted with water. The aqueous phase is alkalized by adding concentrated aqueous ammonium hydroxide solution and extracted with benzene. The organic layer is washed with water, dried over anhydrous sodium sulfate, filtered through a layer consisting of 50 g of aluminium oxide and evaporated. The solution of the residue in anhydrous ether is adjusted to a pH value between 2.5 and 3 by adding ethereal hydrogen chloride solution. The precipitate is filtered and recrystallized from methanol to give the aimed dihydrochloride, m.p.: 191°–192° C.

Analysis: Calculated for $C_{22}H_{27}FN_2O$ (base): C 74.55; H 7.68; F 5.36; N 7.90%; found: C 74.41; H 7.73; F 5.41; N 7.88%.

EXAMPLE 17

The compounds of the invention can be formulated e.g. to the pharmaceutical compositions described hereinafter.

Preparation of tablets 50 g of active ingredient, 92 g of lactose, 40 g of potato starch, 4 g of polyvinylpyrrolidone, 6 g of talc, 1 g of magnesium stearate, 1 g of colloidal silicon dioxide (Aerosil) and 6 g of ultraamylopectin are mixed, granulated as wet and compressed to tablets each of which weighs 200 mg and contains 50 mg of active ingredient which is 1-[2-[bis(4-fluorophenyl)-methoxy]ethyl]-4-(2-propenyl)piperazine dihydrochloride.

Preparation of dragées

The tablets prepared as described above are covered with a coat consisting of sugar and talc, then the dragées are polished by using a mixture of bee wax and carnauba wax.

Each dragée weighs 250 mg.

Preparation of a suspension

The components of 100 ml of suspension are as follows:

| | |
|---|---|
| Active ingredient | 1.0 g |
| Sodium hydroxide | 0.26 g |
| Citric acid | 0.30 g |
| Nipagin (methyl 4-hydroxybenzoate) | 0.10 g |
| Carbopol 940 (polyacrylic acid) | 0.37 g |
| Ethanol (96%) | 1.00 g |
| Raspberry flavour | 0.60 g |
| Sorbitol (70% aqueous solution) | 71.00 g |
| Distilled water for injection purpose q.s. ad | 100 ml |

Carbopol is added in little portions to the solution containing nipagin and citric acid in 20 ml of distilled water under vigorous stirring, then the solution is left to stand for 10 to 12 hours. Thereafter, the amount of sodium hydroxide given above dissolved in 1 ml of distilled water is added, sorbitol is mixed in, finally the ethanolic solution of the raspberry flavour is added while stirring. The active ingredient is added to the vehicle in little portions, then the mixture is transformed to a suspension by means of an immersed homogenizer. Finally, the suspension is filled up to 100 ml with distilled water and the thus-obtained suspension syrup is passed through a colloid mill. The active ingredient is 1-[2-[bis(4-fluorophenyl)methoxy]ethyl]4-(2-propynyl)-piperazine.

We claim:

1. A 1,4-disubstituted piperazine having dopaminergic activity of the formula (I),

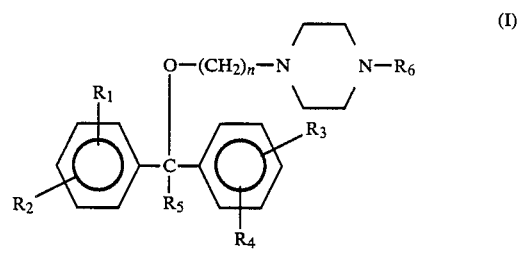

wherein
$R_1$, $R_2$, $R_3$ are the same or different and stand for hydrogen or halogen or a trihalomethyl, lower alkyl, lower alkoxy, nitro, hydroxyl or phenylalkyloxy group,
$R_4$ stands for hydrogen or halogen or a trihalomethyl, lower alkyl, lower alkoxy, nitro, hydroxyl, phenylalkyloxy or an 1-(2-propenyl-4-piperazinyl) group;
$R_5$ stands for hydrogen or a $C_{1-4}$ alkyl group;
$R_6$ represents a $C_{3-6}$ alkenyl or alkynyl group; and
n is 2 or 3,
and pharmaceutically acceptable acid addition salts thereof.

2. A compound selected from the group consisting of 1-[2-[bis(4-fluorophenyl)methoxy]ethyl]-4-(2-propenyl)-piperazine, 1-[2-[(3,4-dichlorophenyl)-phenylmethoxy]ethyl]-4-(2-propenyl)-piperazine, 1-[2-]bis(4-fluorophenyl)methoxy]ethyl]-4-(2-propynyl)-piperazine, and the pharmaceutically acceptable acid addition salts of these compounds.

3. A pharmaceutical composition for treating degenerative and hypofunctional diseases of the dopaminergic system comprising, as active ingredient an effective amount of the 1,4-disubstituted piperazine of claim 1, or a pharmaceutically acceptable acid addition salt thereof in admixture with carriers and/or additives commonly used in the pharmaceutical industry.

4. A method of treating diseases arising from a decrease in the dopamine level which comprises administering to a mammal (including man) in need of such treatment a therapeutically effective amount of the 1,4-disubstituted piperazine of the formula (I),

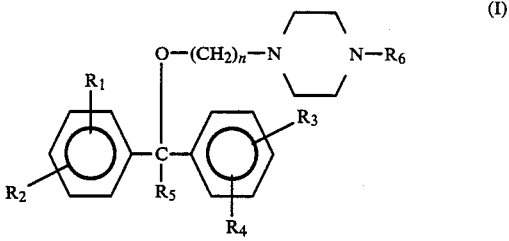

wherein
$R_1$, $R_2$, $R_3$ are the same or different and stand for hydrogen or halogen or a trihalomethyl, lower alkyl, lower alkoxy, nitro, hydroxyl or phenylalkyloxy group;
$R_4$ stands for hydrogen or halogen or a trihalomethyl, lower alkyl, lower alkoxy, nitro, hydroxyl, phenylalkyloxy or an 1-(2-propenyl-4-piperazinyl) group;
$R_5$ stands for hydrogen or a $C_{1-14}$ alkyl group;
$R_6$ represents a $C_{3-6}$ alkenyl or alkynyl group; and
n is 2 or 3,
or a pharmaceutically acceptable acid addition salt.

* * * * *

UNITED STATES PATENT AND TRADEMARK OFFICE
CERTIFICATE OF CORRECTION

PATENT NO. : 4,874,765
DATED : October 17, 1989
INVENTOR(S) : Erzsebet LAPIS et al.

It is certified that error appears in the above-identified patent and that said Letters Patent is hereby corrected as shown below:     Title page:

FOREIGN APPLICATION PRIORITY DATA
should read:

April 28, 1986    [HU]   Hungary... 2251/1749/86

Signed and Sealed this

Fourth Day of September, 1990

Attest:

HARRY F. MANBECK, JR.

*Attesting Officer*    Commissioner of Patents and Trademarks